United States Patent
Narimatsu et al.

(10) Patent No.: US 7,323,324 B2
(45) Date of Patent: Jan. 29, 2008

(54) N-ACETYLGLUCOSAMINE TRANSFERASE, NUCLEIC ACID ENCODING THE SAME, ANTIBODY AGAINST THE SAME AND USE THEREOF FOR DIAGNOSING CANCER OR TUMOR

(75) Inventors: Hisashi Narimatsu, Tsukuba (JP); Niro Inaba, Hachioji (JP); Toshie Iwai, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 358 days.

(21) Appl. No.: 10/492,819

(22) PCT Filed: Oct. 16, 2002

(86) PCT No.: PCT/JP02/10710

§ 371 (c)(1),
(2), (4) Date: Nov. 8, 2004

(87) PCT Pub. No.: WO03/033710

PCT Pub. Date: Apr. 24, 2003

(65) Prior Publication Data

US 2006/0234220 A1 Oct. 19, 2006

(30) Foreign Application Priority Data

Oct. 16, 2001 (JP) .............................. 2001-318676

(51) Int. Cl.
- *C12N 9/10* (2006.01)
- *C12N 1/20* (2006.01)
- *C12N 15/00* (2006.01)
- *C07K 1/00* (2006.01)
- *C07H 21/04* (2006.01)

(52) U.S. Cl. .................. 435/193; 435/183; 435/252.3; 435/320.1; 530/350.1; 536/23.2

(58) Field of Classification Search ................ 435/183, 435/193, 252.3, 320.1; 530/350; 536/23.2
See application file for complete search history.

(56) References Cited

FOREIGN PATENT DOCUMENTS

| WO | WO 01/00848 A1 | 1/2001 |
|----|----------------|--------|
| WO | WO 02/064795   | 8/2002 |

OTHER PUBLICATIONS

Shiraishi et al. Accession BAB21531. Jan. 31, 2001.*
Iwai et al., "Molecular Cloning and Characterization of a Novel UDP-GLCNAC: Galnac-Peptite Beta1, 3-N-Acetylglucosaminyltransferase (Beta3GN-T6), an Enzyme Synthesizing the Core 3 Structure of O-Glycans", J. Biol. Chem., Apr. 12, 2002, 277(15), p. 12802-9.
Vavasseur, F. et al., Synthesis of O-Glycan Core 3: Characterization of UPD-GLCNAC: Galnac-R Beta 3-N-Acetylglucosaminyltransferase Activeity From Colonic Mucosal Tissues and Lack of Activity in Human Cancer Cell Lines, Glycobiology. May 1995, 5(3), p. 351-7.
Brockhausen, I et al., "Mucin Synthesis. UDP-GLCNAC: Galnac-R Beta 3-N-Acetylglucosaminyltransferase and UDP-GLCNAC: GLCNAC Beta 1-3Galnac-R (GLCNAC to Galnac) Beta 6-N-Acetylglucosaminyltransferase From Pig and Rat Colon Mucosa", Biochemistry, Apr. 9, 1985, 24(8), p. 1866-74.
Shiraishi, N. et al., Identification and Characterization of Three Novel Beta 1, 3-N-Acetylglucosaminyltransferases Structurally Related to the Beta 1,3-Galactyosyltransferase Family., J. Biol. Chem., Feb. 2, 2001, 276(5), p. 3498-507.
Togayachi, A. et al., Molecular cloning and Characterization of UDP-GLCNAC: Lactosylceramide Beta 1, 3-N-Acetylglucosaminyltransferase (Beta 3GN-T5), an Essential Enzyme for the Expression of HNK-1 and Lewis X Epitopes on Glycolipids, J. Biol. Chem., Jun. 22, 2001, 276(25), p. 22032-40.
Sasaki, K et al., Expression Cloning of CDNA Encoding a Human Beta-1,3-N-Acetylglucosaminyltransferase That is Essential for Poly-N-Acetyllactosamine Synthesis, Proc. Natl. Acad. Sci., USA, Dec. 23, 1997, 94(26), p. 14294-9.
Zhou, D. et al., "A Beta-1, 3-N-Acetylglucosaminyltransferase With Poly-N-Acetyllactosamine Synthase Activity is Structurally Related to Beta-1, 3-Galactosyltransferases", Proc.Natl. Acad.Sci., USA, Jan. 19, 1999, 96(2), p. 406-11.
Bierhuizen, M.F. et al., "Expression Cloning of a CDNA Encoding UDP-GLCNAC: GAL beta 1-3-Galnac-R (GLCNAC to Galnac) Beta 1-6GLCNAC Transferase by Gene transfer Into CHO Cells Expressing Polyoma Large Tumor Antigen", Proc. Natl. Acad.Sci., USA, Oct. 1, 1992, 89(19), p. 9326-330.

* cited by examiner

*Primary Examiner*—Tekchand Saidha
*Assistant Examiner*—Christian L. Fronda
(74) *Attorney, Agent, or Firm*—Birch, Stewart, Kolasch & Birch, LLP

(57) ABSTRACT

Described are an enzyme having an activity to transfer N-acetylglucosamine to N-acetylgalactosaminyl group through a β1,3-linkage; nucleic acid coding for the enzyme; and method for diagnosis of a cancer and/or tumor, especially a cancer and/or tumor of a digestive organ using the expression amount of the gene of the enzyme as an index. A gene coding for a novel enzyme having an activity to transfer N-acetylglucosamine to N-acetylgalactosaminyl group through the β1,3-linkage was cloned from human colon and stomach cells, and the gene was sequenced. The enzyme was expressed, and a monoclonal antibody to the enzyme was prepared. Since this enzyme is not produced substantially or at all in cancer and/or tumor cells, especially in cancer or tumor cells of a digestive organ, the cancer and/or tumor may be diagnosed using the expression of the gene of the enzyme as an index.

3 Claims, No Drawings

SEQUENCE LISTING

<160> NUMBER OF SEQ ID NOS: 13

<210> SEQ ID NO 1
<211> LENGTH: 384
<212> TYPE: PRT
<213> ORGANISM: Homo sapiens

<400> SEQUENCE: 1

```
Met Ala Phe Pro Cys Arg Arg Ser Leu Thr Ala Lys Thr Leu Ala Cys
1               5                   10                  15

Leu Leu Val Gly Val Ser Phe Leu Ala Leu Gln Gln Trp Phe Leu Gln
            20                  25                  30

Ala Pro Arg Ser Pro Arg Glu Glu Arg Ser Pro Gln Glu Glu Thr Pro
        35                  40                  45

Glu Gly Pro Thr Asp Ala Pro Ala Asp Glu Pro Pro Ser Glu Leu
    50                  55                  60

Val Pro Gly Pro Pro Cys Val Ala Asn Ala Ser Ala Asn Ala Thr Ala
65                  70                  75                  80

Asp Phe Glu Gln Leu Pro Ala Arg Ile Gln Asp Phe Leu Arg Tyr Arg
                85                  90                  95

His Cys Arg His Phe Pro Leu Leu Trp Asp Ala Pro Ala Lys Cys Ala
            100                 105                 110

Gly Gly Arg Gly Val Phe Leu Leu Leu Ala Val Lys Ser Ala Pro Glu
```

```
                115                 120                 125
His Tyr Glu Arg Arg Glu Leu Ile Arg Arg Thr Trp Gly Gln Glu Arg
    130                 135                 140

Ser Tyr Gly Gly Arg Pro Val Arg Arg Leu Phe Leu Gly Thr Pro
145                 150                 155                 160

Gly Pro Glu Asp Glu Ala Arg Ala Glu Arg Leu Ala Glu Leu Val Ala
                165                 170                 175

Leu Glu Ala Arg Glu His Gly Asp Val Leu Gln Trp Ala Phe Ala Asp
            180                 185                 190

Thr Phe Leu Asn Leu Thr Leu Lys His Leu His Leu Leu Asp Trp Leu
        195                 200                 205

Ala Ala Arg Cys Pro His Ala Arg Phe Leu Leu Ser Gly Asp Asp Asp
    210                 215                 220

Val Phe Val His Thr Ala Asn Val Val Arg Phe Leu Gln Ala Gln Pro
225                 230                 235                 240

Pro Gly Arg His Leu Phe Ser Gly Gln Leu Met Glu Gly Ser Val Pro
                245                 250                 255

Ile Arg Asp Ser Trp Ser Lys Tyr Phe Val Pro Pro Gln Leu Phe Pro
            260                 265                 270

Gly Ser Ala Tyr Pro Val Tyr Cys Ser Gly Gly Phe Leu Leu Ser
        275                 280                 285

Gly Pro Thr Ala Arg Ala Leu Arg Ala Ala Arg His Thr Pro Leu
    290                 295                 300

Phe Pro Ile Asp Asp Ala Tyr Met Gly Met Cys Leu Glu Arg Ala Gly
305                 310                 315                 320

Leu Ala Pro Ser Gly His Glu Gly Ile Arg Pro Phe Gly Val Gln Leu
                325                 330                 335

Pro Gly Ala Gln Gln Ser Ser Phe Asp Pro Cys Met Tyr Arg Glu Leu
            340                 345                 350

Leu Leu Val His Arg Phe Ala Pro Tyr Glu Met Leu Leu Met Trp Lys
        355                 360                 365

Ala Leu His Ser Pro Ala Leu Ser Cys Asp Arg Gly His Arg Val Ser
    370                 375                 380

<210> SEQ ID NO 2
<211> LENGTH: 1155
<212> TYPE: DNA
<213> ORGANISM: Homo sapiens
<220> FEATURE:
<221> NAME/KEY: CDS
<222> LOCATION: (1)..(1152)

<400> SEQUENCE: 2 atg gct ttt ccc tgc cgc agg tcc ctg act gcc aag act ctg gcc tgc    48
Met Ala Phe Pro Cys Arg Arg Ser Leu Thr Ala Lys Thr Leu Ala Cys
1               5                   10                  15 ctc ctg gtg ggc gtg agt ttc tta gca ctg cag cag tgg ttc ctc cag    96
Leu Leu Val Gly Val Ser Phe Leu Ala Leu Gln Gln Trp Phe Leu Gln
            20                  25                  30 gcg cca agg tcc ccg cgg gag gag agg tcc ccg cag gag gag acg cca   144
Ala Pro Arg Ser Pro Arg Glu Glu Arg Ser Pro Gln Glu Glu Thr Pro
        35                  40                  45 gag ggt ccc acc gac gct ccc gcg gct gac gag ccg ccc tcg gag ctc   192
Glu Gly Pro Thr Asp Ala Pro Ala Ala Asp Glu Pro Pro Ser Glu Leu
    50                  55                  60 gtc ccc ggg ccc ccg tgc gtg gcg aac gcc tcg gcg aac gcc acg gcc   240
Val Pro Gly Pro Pro Cys Val Ala Asn Ala Ser Ala Asn Ala Thr Ala
```

```
                65                  70                  75                  80
gac ttc gag cag ctg ccc gcg cgc atc cag gac ttc ctg cgg tac cgc         288
Asp Phe Glu Gln Leu Pro Ala Arg Ile Gln Asp Phe Leu Arg Tyr Arg
                    85                  90                  95 cac tgc cgc cac ttc ccg ctg ctt tgg gac gca ccg gcc aag tgc gcc         336
His Cys Arg His Phe Pro Leu Leu Trp Asp Ala Pro Ala Lys Cys Ala
               100                 105                 110 ggc ggc cga ggc gtg ttc ctg ctc ctg gcg gtg aag tcg gcg cct gag         384
Gly Gly Arg Gly Val Phe Leu Leu Leu Ala Val Lys Ser Ala Pro Glu
           115                 120                 125 cac tac gag cga cgc gag ctc atc cgg cgc acg tgg ggg caa gag cgc         432
His Tyr Glu Arg Arg Glu Leu Ile Arg Arg Thr Trp Gly Gln Glu Arg
       130                 135                 140 agc tac ggc ggg cgg cca gtg cgc cgc ctc ttt cta ttg ggc acc ccg         480
Ser Tyr Gly Gly Arg Pro Val Arg Arg Leu Phe Leu Leu Gly Thr Pro
145                 150                 155                 160 ggc ccc gag gac gag gcg cgc gcg gag cgg ctg gcg gag ctg gtg gcg         528
Gly Pro Glu Asp Glu Ala Arg Ala Glu Arg Leu Ala Glu Leu Val Ala
                    165                 170                 175 ctg gag gcg cgc gag cac ggc gac gtg ctg cag tgg gcc ttc gcg gac         576
Leu Glu Ala Arg Glu His Gly Asp Val Leu Gln Trp Ala Phe Ala Asp
               180                 185                 190 acc ttc ctc aac ctc acg ctc aag cac ctg cac ttg ctc gac tgg ctg         624
Thr Phe Leu Asn Leu Thr Leu Lys His Leu His Leu Leu Asp Trp Leu
           195                 200                 205 gct gca cgc tgc ccg cac gcg cgc ttt ctg ctc agc ggc gac gac gac         672
Ala Ala Arg Cys Pro His Ala Arg Phe Leu Leu Ser Gly Asp Asp Asp
       210                 215                 220 gtg ttc gtg cac acc gcc aac gta gtc cgc ttc ctg cag gcg cag cca         720
Val Phe Val His Thr Ala Asn Val Val Arg Phe Leu Gln Ala Gln Pro
225                 230                 235                 240 ccc ggc cgc cac ctg ttc tcc ggc cag ctc atg gag ggc tcc gtg ccc         768
Pro Gly Arg His Leu Phe Ser Gly Gln Leu Met Glu Gly Ser Val Pro
                    245                 250                 255 atc cgc gac agc tgg agc aag tac ttc gtg ccg ccg cag ctc ttc ccc         816
Ile Arg Asp Ser Trp Ser Lys Tyr Phe Val Pro Pro Gln Leu Phe Pro
               260                 265                 270 ggg tcc gct tac ccg gtg tac tgc agc ggc ggc ggc ttc ctc ctg tcc         864
Gly Ser Ala Tyr Pro Val Tyr Cys Ser Gly Gly Gly Phe Leu Leu Ser
           275                 280                 285 ggc ccc acg gcc cgg gcc ctg cgc gcg gcc gcc cgc cac acc ccg ctc         912
Gly Pro Thr Ala Arg Ala Leu Arg Ala Ala Ala Arg His Thr Pro Leu
       290                 295                 300 ttc ccc atc gac gac gcc tac atg ggc atg tgt ctg gag cgc gcc ggc         960
Phe Pro Ile Asp Asp Ala Tyr Met Gly Met Cys Leu Glu Arg Ala Gly
305                 310                 315                 320 ctg gcg ccc agc ggc cac gag ggc atc cgg ccc ttc ggc gtg cag ctg        1008
Leu Ala Pro Ser Gly His Glu Gly Ile Arg Pro Phe Gly Val Gln Leu
                    325                 330                 335 cct ggc gca cag cag tcc tcc ttc gac ccc tgc atg tac cgc gag ttg        1056
Pro Gly Ala Gln Gln Ser Ser Phe Asp Pro Cys Met Tyr Arg Glu Leu
               340                 345                 350 ctg cta gtg cac cgc ttc gcg ccc tac gag atg ctg ctc atg tgg aag        1104
Leu Leu Val His Arg Phe Ala Pro Tyr Glu Met Leu Leu Met Trp Lys
           355                 360                 365 gcg ctg cac agc ccc gcg ctc agc tgt gac cgg gga cac cgg gtc tcc        1152
Ala Leu His Ser Pro Ala Leu Ser Cys Asp Arg Gly His Arg Val Ser
       370                 375                 380 tga                                                                    1155
```

```
<210> SEQ ID NO 3
<211> LENGTH: 24
<212> TYPE: DNA
<213> ORGANISM: Artificial Sequence
<220> FEATURE:
<223> OTHER INFORMATION: Oligonucleotide primer used in PCR for
      amplifying beta3GnT-6 cDNA

<400> SEQUENCE: 3
ctccagacac atgcccatgt aggc                                          24

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide primer used in PCR for
      amplifying beta3GnT-6 cDNA

<400> SEQUENCE: 4
gtcgtcgtcg ccgctgagca gaaa                                          24

<210> SEQ ID NO 5
<211> LENGTH: 51
<212> TYPE: DNA
<213> ORGANISM: Artificial Sequence
<220> FEATURE:
<223> OTHER INFORMATION: Oligonucleotide primer used in PCR for
      amplifying beta3GnT-6 cDNA

<400> SEQUENCE: 5
ggggacaagt ttgtacaaaa aagcaggctt ccaggaggag acgccagagg g            51

<210> SEQ ID NO 6
<211> LENGTH: 50
<212> TYPE: DNA
<213> ORGANISM: Artificial Sequence
<220> FEATURE:
<223> OTHER INFORMATION: Oligonucleotide primer used in PCR for
      amplifying beta3GnT-6 cDNA

<400> SEQUENCE: 6
ggggaccact ttgtacaaga aagctgggtc tggcctcagg agacccggtg              50

<210> SEQ ID NO 7
<211> LENGTH: 88
<212> TYPE: DNA
<213> ORGANISM: Artificial Sequence
<220> FEATURE:
<223> OTHER INFORMATION: template used in PCR employed in preparation
      of expression vector
<220> FEATURE:
<221> NAME/KEY: CDS
<222> LOCATION: (5)..(88)

<400> SEQUENCE: 7 gatc atg cat ttt caa gtg cag att ttc agc ttc ctg cta atc agt gcc   49
     Met His Phe Gln Val Gln Ile Phe Ser Phe Leu Leu Ile Ser Ala
     1               5                   10                  15 tca gtc ata atg tca cgt gga cat cac cat cac cat cac                 88
Ser Val Ile Met Ser Arg Gly His His His His His His
            20                  25

<210> SEQ ID NO 8
<211> LENGTH: 26
```

```
<212> TYPE: DNA
<213> ORGANISM: Artificial Sequence
<220> FEATURE:
<223> OTHER INFORMATION: Oligonucleotide primer used in PCR employed
      in preparation of expression vector

<400> SEQUENCE: 8
cgggatccat gcattttcaa gtgcag                                          26

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide primer used in PCR employed
      in preparation of expression vector

<400> SEQUENCE: 9
ggaattcgtg atggtgatgg tgatg                                           25

<210> SEQ ID NO 10
<211> LENGTH: 94
<212> TYPE: DNA
<213> ORGANISM: Artificial Sequence
<220> FEATURE:
<223> OTHER INFORMATION: template used in PCR employed in preparation of
      expression vector FEATURE:
<221> NAME/KEY: CDS
<222> LOCATION: (5)..(94)

<400> SEQUENCE: 10 gatc atg cat ttt caa gtg cag att ttc agc ttc ctg cta atc agt gcc     49
     Met His Phe Gln Val Gln Ile Phe Ser Phe Leu Leu Ile Ser Ala
     1               5                  10                  15 tca gtc ata atg tca cgt gga gat tac aag gac gac gat gac aag          94
Ser Val Ile Met Ser Arg Gly Asp Tyr Lys Asp Asp Asp Asp Lys
            20                  25                  30

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide primer used in PCR employed
      in preparation of expression vector

<400> SEQUENCE: 11
ggaattcttg tcatcgtcgt ccttg                                           25

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer used in PCR for
      amplifying beta3GnT-6 cDNA

<400> SEQUENCE: 12
gcctacatgg gcatgtgtct ggag                                            24

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide primer used in PCR for
      amplifying beta3GnT-6 cDNA
```

```
<400> SEQUENCE: 13
agagctgggc aggacgtaag gtac                                            24
```

N-ACETYLGLUCOSAMINE TRANSFERASE, NUCLEIC ACID ENCODING THE SAME, ANTIBODY AGAINST THE SAME AND USE THEREOF FOR DIAGNOSING CANCER OR TUMOR

Novel N-Acetylglucosamine Transferase, Nucleic Acid Encoding the Same, Antibody against the same, and Use Thereof for Diagnosing Cancer or Tumor

TECHNICAL FIELD

The present invention relates to a novel enzyme having an activity to transfer N-acetylglucosamine to a non-reducing terminal of N-acetylgalactosaminyl group through a β1,3-linkage, and to a nucleic acid coding for the same, as well as to nucleic acids for measuring the nucleic acid. The present invention further relates to an antibody which undergoes antigen-antibody reaction with the enzyme, use thereof for diagnosis of a cancer or tumor, and to diagnosis of cancer or tumor using the expression amount of the gene of the enzyme as an index.

BACKGROUND ART

Although the activity per se of an enzyme which synthesizes core 3 sugar chain (N-acetylglucosaminyl β1,3N-acetylgalactosaminylα1-R; GlcNAcβ1-3GalNAcα1-R), which transfers N-acetylglucosamine to a non-reducing terminal of N-acetylgalactosaminyl group is known, the enzyme has not been isolated or identified. Therefore, to prepare or produce the core 3 sugar chain structure, it is necessary to chemically synthesize the structure, isolating the structure from a biological component or to synthesize the structure enzymatically using a tissue homogenate. Further, it has been reported that although this enzyme activity exists in normal digestive tract, the activity is lost in established cell lines originated from digestive tract. This means that although the enzyme exists in normal digestive tract, the activity of the enzyme is thought to be reduced in abnormal tissues such as cancers and digestive tract polyps. Therefore, to examine the change in the expression amount of the enzyme or to examine the core 3 sugar chain is important for diagnoses and therapies.

By isolating an enzyme having an activity to transfer N-acetylglucosamine to N-acetylgalactosaminyl group through β1,3-linkage, and by characterizing the structure of the gene, production of the enzyme by genetic engineering process and diagnosis of cancer and the like based on the gene may be attained. However, the enzyme has not yet been purified or isolated, and there is no clue to the isolation of the enzyme and identification of the gene. As a result, an antibody to the enzyme has not been prepared.

DISCLOSURE OF THE INVENTION

Accordingly, an object of the present invention is to provide an enzyme having an activity to transfer N-acetylglucosamine to N-acetylgalactosaminyl group through the β1,3-linkage, and a nucleic acid coding for the same. Another object of the present invention is to provide a recombinant vector which expresses the above-mentioned the nucleic acid in a host cell, and to provide a cell in which the nucleic acid is introduced and which expresses the nucleic acid and the enzyme protein. The expressed enzyme protein may be used for the preparation of an antibody and provides a production process of the enzyme protein. Further, the enzyme protein may also be used for immunohistochemical staining and immunoassays such as RIA and EIA that use the expressed enzyme protein and the antibody to the enzyme protein. Still another object of the present invention is to provide a nucleic acid for measurement of the nucleic acid according to the present invention. Still another object of the present invention is to provide an antibody which undergoes antigen-antibody reaction with the enzyme. Still another object of the present invention is to provide diagnosis and a reagent which is used therefor for cancers and tumors, especially for cancers and tumors of digestive tract.

As mentioned above, since the enzyme of interest has not been isolated, it is impossible to know its partial amino acid sequence. In general, it is not easy to isolate and purify a protein contained in cells in a trace amount, and so isolation of the enzyme from cells, which has not been isolated so far is expected not easy. The present inventors thought that if there is a homologous region among the nucleotide sequences of the various enzyme genes, which enzymes have relatively similar actions to that of the enzyme of interest, the gene of the enzyme of interest may also have the homologous sequence. After searching the nucleotide sequences of the known β1,3-N-acetylglucosaminyltransferase genes, β1,3-galactoslytransferase genes and β1,3-N-acetylgalactosaminyltransferase genes, a homologous region was discovered. Thus, based on the cloning by PCR using cDNA library, in which a primer was set in the homologous region, and after various considerations, the present inventors succeeded in the cloning of the gene of the enzyme, and its nucleotide sequence and the deduced amino acid sequence were determined, thereby accomplishing the present invention. Further, the cloned gene was expressed to obtain the enzyme, and a monoclonal antibody to the enzyme was prepared using the enzyme as an antigen. Further, using this monoclonal antibody, cancers and polyps of colon and stomach were immunohistochemical-stained to confirm that the enzyme is expressed in normal colon and stomach, but is not expressed in most cases in cancers and advanced polyps. As a result, the present inventors discovered that diagnosis of cancers or tumors may be attained using the expression amount of the gene of the enzyme.

That is, the present invention provides a protein having the amino acid sequence shown in SEQ ID NO:1 in SEQUENCE LISTING, or a protein having the same amino acid sequence as shown in SEQ ID NO:1 except that 1 or more amino acids are substituted or deleted, or that one or more amino acids are inserted or added, which has an activity to transfer N-acetylglucosamine to N-acetylgalactosaminyl group through the β1,3-linkage. The present invention also provides a nucleic acid coding for the protein according to the present invention. The present invention also provides a recombinant vector containing the nucleic acid according to the present invention, which can express the nucleic acid in a host cell. The present invention further provides a cell into which the nucleic acid according to the present invention is introduced, which expresses the nucleic acid. The present invention still further provides a nucleic acid for measurement of the above-mentioned nucleic acid, which specifically hybridizes with the above-mentioned nucleic acid. The present invention still further provides use of the nucleic acid for measurement for the diagnosis of a cancer or tumor. The present invention still further provides an antibody or an antigen-binding fragment thereof, which undergoes antigen-antibody reaction with the protein according to the present invention, as well as use thereof for the diagnosis of a cancer or tumor. The present invention still further provides a method for diagnosis of a cancer and/or tumor, comprising determining expression amount of the gene coding for the protein according to the present invention, in (a) sample cell(s) separated from body. The present invention still further provides a method for measuring the nucleic acid according to the present invention, comprising hybridizing the nucleic acid for measurement of nucleic acid, according to the present invention and the nucleic acid according to the present invention by annealing, and measuring the hybridized nucleic acid. The present invention still further provides a method for diagnosis of a cancer and/or tumor, comprising subjecting the antibody or the antigen-binding fragment thereof according to the present invention and the enzyme according to the present invention in (a) sample cell(s) and/or on (a) sample cell(s) to antigen-antibody reaction, and measuring the bound antigen or the antigen-binding fragment thereof or the enzyme. The present invention still further provides a use of the nucleic acid for measurement of the nucleic acid, according to the present invention, for the production of nucleic acid for measurement of the nucleic acid according to the present invention. The present invention still further provides a use of the antibody or the antigen-binding fragment thereof according to the present invention, for the production of diagnostic reagent for a cancer and/or tumor.

By the present invention, an enzyme having an activity to transfer N-acetylglucosamine to N-acetylgalactosaminyl group through the β1,3-linkage, and the nucleic acid coding for the enzyme were first provided. Further, by the present invention, a nucleic acid for measurement of the nucleic acid and an antibody which undergoes antigen-antibody reaction with the enzyme were first provided. Still further, by the present invention, a simple and accurate method for diagnosis of a cancer or tumor, especially a cancer or tumor of a digestive organ, and the nucleic acid for measurement and antibody used therefor were first provided. Therefore, it is expected that the present invention will greatly contribute to the diagnosis of cancers and tumors of digestive organs.

BEST MODE FOR CARRYING OUT THE PRESENT INVENTION

The nucleic acid coding for the protein according to the present invention, which was cloned by the method described in detail in the Examples below, has the nucleotide sequence shown in SEQ ID NO:2 in SEQUENCE LISTING, and the deduced amino acid sequence encoded thereby is shown under the nucleotide sequence. SEQ ID NO:1 shows the amino acid sequence alone.

The protein (designated "β3Gn-T6") according to the present invention obtained in the Examples below is an enzyme having the following properties:

Each of the properties as well as measuring methods thereof is described in detail in the Examples below.

Action: Transfer N-acetylglucosamine to a non-reducing terminal of N-acetylgalactosaminyl group (EC 2.4.1.147, Acetylgalactosaminyl-O-glycosyl-glycoprotein β1,3-N-acetylglucosaminyltransferase). The reaction catalyzed by the enzyme, expressed in terms of reaction equation, is as follows: UDP-N-acetyl-D-glucosamine+N-acetyl-D-galactosaminyl-R → UDP+N-acetyl-β-D-glucosaminylβ1,3-N-acetyl-D-galactosaminyl-R(GalNAc-R+UDP-GlcNAc → GlcNAcβ1,3-GalNAc-R+UDP)

Substrate Specificity: N-acetylgalactosaminyl group, for example, N-acetylgalactosaminyl α1-R (R represents a residue of ester bond with a hydroxyl group in the side chain of serine or threonine in protein or a hydroxyl group of p-nitrophenyl or the like).

In general, it is well-known in the art that there are cases wherein the physiological activity of a physiologically active protein such as an enzyme is retained even if the amino acid sequence of the protein is modified such that one or more amino acids in the amino acid sequence is substituted or deleted, or one or more amino acids are inserted or added to the amino acid sequence. Therefore, a protein having the same amino acid sequence as shown in SEQ ID NO:1 except that one or more amino acids are substituted or deleted, or one or more amino acids are inserted or added, which protein has an activity to transfer N-acetylglucosamine to a non-reducing group of N-acetylgalactosaminyl group through the β1,3-linkage (the protein is hereinafter referred to as "modified protein" for convenience) is also within the scope of the present invention. The amino acid sequence of such a modified protein preferably has a homology of not less than 70%, preferably not less than 90%, still more preferably not less than 95% to the amino acid sequence shown in SEQ ID NO:1. The homology of the nucleotide sequence may easily be calculated by using a well-known software such as FASTA, and such a software is available on the internet. Further, as the modified protein, one having the same amino acid sequence as shown in SEQ ID NO:1 except that one or a several amino acids are substituted or deleted, or that one or several amino acids are inserted or added is especially preferred.

The present invention also provides the nucleic acid coding for the amino acid sequence as shown in SEQ ID NO:1 and nucleic acids coding for the amino acid sequences of the above-mentioned modified proteins. As the nucleic acid, DNA is preferred. As is well-known, due to degeneracy, there may be a plurality of codons each of which codes for the same single amino acid. However, as long as a nucleic acid codes for the above-described amino acid sequence, any nucleic acid having any nucleotide sequence is within the scope of the present invention. The nucleotide sequence of the cDNA actually cloned in the Examples below is shown in SEQ ID NO:2. Those nucleic acids which hybridize with the nucleic acid having the nucleotide sequence shown in SEQ ID NO:2 under stringent conditions (i.e., hybridization is performed at 50 to 65° C. using a common hybridization solution such as 5×Denhardt's reagent, 6×SSC, 0.5% SDS or 0.1% SDS), and which code for the above-described modified proteins are within the scope of the present invention.

By inserting the above-described nucleic acid according to the present invention into a cloning site of an expression vector, a recombinant vector which can express the above-described nucleic acid in a host cell may be obtained. As the expression vector, various plasmid vectors and virus vectors for various host cells are well-known and commercially available. In the present invention, such a commercially available expression vector may preferably be employed. The methods for transforming or transducing host cells with such a recombinant vector are also well-known. The present invention also provides a cell into which the nucleic acid according to the present invention is introduced by transformation, transduction or transfection, which expresses the nucleic acid. The methods per se for introducing a foreign gene into a host cell are well-known, and the introduction of the foreign gene may easily be attained by, for example, using the above-mentioned recombinant vector. An example of the construction of a recombinant vector and a method for introducing the nucleic acid according to the present invention into host cells using the recombinant vector are described in detail in the Examples below.

Sugar chains may be bound to the protein according to the present invention, as long as the protein has the amino acid sequence described above and has the above-described enzyme activity. In other words, the term "protein" used herein also includes "glycoprotein".

Since the nucleotide sequence of the cDNA of the novel enzyme according to the present invention was clarified by the present invention, nucleic acids for measurement according to the present invention (hereinafter referred to as simply "nucleic acid for measurement"), which hybridize with the mRNA or the cDNA of the enzyme under stringent conditions (described above), were provided by the present invention. Although it is preferred, in general, that the nucleic acid for measurement has a sequence homologous with a part of the nucleic acid having the nucleotide sequence shown in SEQ ID NO:2, mismatch of about 1 or 2 bases does not matter in many cases. The nucleic acid for measurement may be used as a probe or a primer in a nucleic acid-amplification method. To assure specificity, the number of bases in the nucleic acid for measurement is preferably not less than 15, more preferably not less than 18. In cases where the nucleic acid is used as a probe, the size is preferably not less than 15 bases, more preferably not less than 20 bases, and not more than the full length (1152 bases) of the coding region. In cases where the nucleic acid is used as a primer, the size is preferably not less than 15 bases, more preferably not less than 18 bases, and less than 50 bases. The methods for measuring a test nucleic acid using a nucleic acid having a sequence complementary to a part of the test nucleic acid as a primer of a gene-amplification method such as PCR or as a probe are well-known, and the methods by which the mRNA of the enzyme according to the present invention was measured by Northern blot or in situ hybridization are concretely described in detail in the Examples below. In the present specification, "measurement" includes detection, quantification and semi-quantification.

The nucleic acid-amplification methods such as PCR are well-known in the art, and reagent kits and apparatuses therefor are commercially available, so that they may easily be carried out. That is, for example, a test nucleic acid serving as a template (e.g., the cDNA of the gene of the enzyme of the present invention) and a pair of nucleic acids for measurement (primers) according to the present invention are mixed in a buffer in the presence of Taq polymerase and dNTPs, and the steps of denaturation, annealing and extension are carried out by changing the temperature of the reaction mixture. Usually, the denaturation step is carried out at 90 to 95° C., the annealing step is carried out at Tm between the template and the primers or a vicinity thereof (preferably within ±4° C.), and the extension step is carried out at 72° C. which is the optimum temperature of Taq polymerase. The reaction time of each step is selected from about 30 seconds to 2 minutes. By repeating this thermal cycle for about 25 to 40 times, the region between the pair of primers is amplified. The nucleic acid-amplification method is not restricted to PCR, but other nucleic acid-amplification methods well-known in the art may also be employed. By carrying out the nucleic acid-amplification method using a pair of the above-described nucleic acids for measurement according to the present invention as primers and using the test nucleic acid as a template, the test nucleic acid is amplified. In contrast, in cases where the test nucleic acid is not contained in the sample, the amplification does not occur. Therefore, by detecting the amplification product, whether the test nucleic acid exists in the sample or not may be determined. Detection of the amplification product may be carried out by a method in which the reaction solution after the amplification is subjected to electrophoresis, and the bands are stained with ethidium bromide or the like, or by a method in which the amplification product after electrophoresis is immobilized on a solid phase such as a nylon membrane, a labeled probe which specifically hybridizes with the test nucleic acid is hybridized with the test nucleic acid, and the label after washing is detected. Alternatively, the test nucleic acid in the sample may be quantified by the so called realtime detection PCR using a quencher fluorescent pigment and a reporter fluorescent pigment. Since the kits for realtime detection PCR are also commercially available, realtime detection PCR may also be carried out easily. The test nucleic acid may also be semi-quantified based on the intensity of the band resulted in electrophoresis. The test nucleic acid may be a mRNA or a cDNA reverse-transcribed from a mRNA. In cases where a mRNA is amplified as the test nucleic acid, NASBA method (3SR method, TMA method) using the above-described pair of primers may also be employed. NASBA method per se is well-known, and kits therefor are commercially available, so that NASBA method may easily be carried out using the above-described pair of primers.

As the probe, labeled probe obtained by labeling the above-described nucleic acid for measurement with a fluorescent label, radioactive label, biotin label or the like may be used. The methods per se for labeling a nucleic acid are well-known. Whether the test nucleic acid exists in the sample or not may be determined by immobilizing the test nucleic acid or amplification product thereof, hybridizing the labeled probe therewith, and measuring the label bound to the solid phase after washing. Alternatively, the nucleic acid for measurement is immobilized, the test nucleic acid is hybridized therewith, and the test nucleic acid bound to the solid phase is detected by a labeled probe or the like. In such a case, the nucleic acid for measurement immobilized on the solid phase is also called a probe. The methods for measuring a test nucleic acid using a nucleic acid probe are also well-known in the art, and may be attained by making contact between the nucleic acid probe and the test sample in a buffer at Tm or a vicinity thereof (preferably within ±4° C.) so as to hybridize them, and then measuring the hybridized labeled probe or the test nucleic acid bound to the immobilized probe. Such a method includes well-known methods such as Northern blot and in situ hybridization described in the Examples below, as well as Southern blot.

By making the enzyme according to the present invention act on a glycoprotein, oligosaccharide or polysaccharide having (an) N-acetylgalactosaminyl group(s), N-acetylglucosamine is bound through the β1,3-linkage. Thus, the enzyme according to the present invention may be used for modification of sugar chains of glycoproteins and for synthesis of saccharides. Further, by administering this enzyme as an immunogen to an animal, an antibody to this enzyme may be prepared, so that the enzyme may be measured by an immunoassay using the antibody. Therefore, the enzyme according to the present invention and the nucleic acid coding for the enzyme are useful for the preparation of such an immunogen. It is known that the activity of the enzyme in cell lines originated from digestive organs (such as stomach and colon) is decreased (Glycobiology Vol.5, No3, 351-357, 1995 Vavasseur, F., Yang, J-M., Dole, K., Paulsen, H. and Brockhausen, I). Therefore, by determining the amount of the mRNA of the enzyme of the present invention in colon cells using the nucleic acid for measurement according to the present invention, cancers of digestive organs such as stomach cancer and colon cancer may be diagnosed. Recently, structures of sugar chains in normal colon tissue were reported (Biochem.J. 358, 657-664, 2001 Capon, C., Maes, E., Michalski, J-C., Leffler, H. and Kim, Y.S). According to this report, the glycans bound to mucin of normal colon tissue comprise core 3 structures as the main products, and sugar chains are extended from the core 3 structures to form Sda/Cad-antigen-like structures. Thus, it is thought that the sugar chains of core 3 structures are very important physiologically in the normal colon tissue, and it is very important to examine the core 3 synthetase (the enzyme of the present invention) and the change in the sugar chains of the core 3 structures. The enzyme may be immunologically detected by using an antibody prepared using the enzyme.

As will be described concretely in the Examples below, the present inventors produced the above-described enzyme according to the present invention by a genetic engineering process, and prepared a monoclonal antibody which undergoes antigen-antibody reaction with the enzyme, using the produced enzyme as an immunogen. The hybridoma (MA-136 G8 NO.144'02. 10.1) producing the monoclonal antibody has been deposited with International Patent Organism Depositary, National Institute of Advanced Industrial Science and Technology, at AIST Tsukuba Central 6, 1-1-1 Higashi, Tsukuba, Ibaraki, Japan, under an accession No. FERM BP-8200 as of Oct. 4, 2002, under the Budapest Treaty. Further, as will be described concretely in the Examples below, immunohistostaining using the obtained monoclonal antibody revealed that the enzyme is detected in the normal tissues in stomach and colon, while it is not substantially detected in cancers and tumors (polyps) of a grade of atypism of 4 or more. Therefore, the antibody, preferably the monoclonal antibody, which undergoes antigen-antibody reaction with the enzyme of the present invention may be used for the diagnosis of cancers or tumors, preferably cancers or tumors of digestive tract, especially cancers or tumors of stomach or colon, more preferably stomach cancer or colon cancer. In cases where the antibody is used for the diagnosis of a cancer or tumor, the above-described enzyme is measured by an immunoassay utilizing the antigen-antibody reaction between the enzyme in the sample cells and the antibody, and the result is compared with the measurement results obtained for normal cells. If the measured amount of the enzyme is smaller than that in the normal cells, especially if the enzyme is not detected, it is judged that the possibility that the sample is a cancer or tumor is high. The immunoassays per se are well-known, and any of the well-known immunoassays may be employed. That is, classifying the known immunoassays according to the reaction type, known immunoassays include sandwich immunoassays, competition immunoassays, agglutination immunoassays, Western blot and the like. Classifying the known immunoassays according to the label employed, known immunoassays include fluorescence immunoassays, enzyme immunoassays, radio immunoassays, biotin immunoassays and the like. Any of these immunoassays may be employed. Further, diagnosis may be attained by immunohistostaining. In cases where a labeled antibody is used in the immunoassay, the methods per se for labeling a nucleic acid are well-known, and any of the well-known methods may be employed. It is known that by decomposing an antibody with papain or pepsin, an antibody fragment such as Fab fragment or F(ab')$_2$ fragment having the binding ability with the corresponding antigen (such a fragment is called "antigen-binding fragment" in the present specification) is obtained. The antigen-binding fragments of the antibody of the present invention may also be used in the same manner as the antibody.

These immunoassays per se are well-known in the art, and so it is not necessary to explain these immunoassays in the present specification. Briefly, in sandwich immunoassays, for example, the antibody of the present invention or an antigen-binding fragment thereof is immobilized on a solid phase as a first antibody. The first antibody is then reacted with a sample, and after washing the solid phase, the resultant is then reacted with a second antibody which reacts with the enzyme of the present invention by antigen-antibody reaction. After washing the solid phase, the second antibody bound to the solid phase is measured. By labeling the second antibody with an enzyme, fluorescent substance, radioactive substance, biotin or the like, measurement of the second antibody bound to the solid phase may be attained by measuring the label. The above-mentioned measurement is conducted for a plurality of standard samples each containing a known concentration of the enzyme, and the relationship between the concentrations of the enzyme in the standard samples and the measured amounts of the label is plotted to prepare a calibration curve. The enzyme in a test sample may be quantified by applying the measured amount to the calibration curve. It should be noted that the above-mentioned first antibody and the above-mentioned second antibody may be exchanged. In agglutination immunoassays, the antibody according to the present invention or an antigen-binding fragment thereof is immobilized on particles such as latex particles, and the particles are reacted with a sample, followed by measurement of the absorbance. The above-mentioned measurement is conducted for a plurality of standard samples each containing a known concentration of the enzyme, and the relationship between the concentrations of the enzyme in the standard samples and the measured absorbance is plotted to prepare a calibration curve. The enzyme in a test sample may be determined by applying the measured absorbance to the calibration curve.

The reagents necessary for each type of immunoassay are also well-known in the art. Except for the antibody used, the immunoassay according to the present invention may be carried out using an ordinary kit for immunoassay. For example, such an immunoassay kit may usually include buffer solution, solid phase, labeled second antibody and the like.

As will be concretely described in the Examples below, it was confirmed that diagnosis of cancers or tumors can be attained by using the amount of expression of the enzyme of the present invention as an index. Thus, the present invention also provides a method for diagnosis of a cancer or tumor, comprising determining the amount of expression of the gene coding for the enzyme of the present invention, in (a) sample cell(s) separated from body. As will be concretely described in the Examples below, the tumors which can be detected by the diagnosis method according to the present invention are cancers or tumors for which cancers are strongly suspected. As the sample cells, cells of digestive organs are preferred, and cells from colon or stomach are especially preferred. By applying the diagnosis method to these cells, cancers or tumors of digestive organs, especially cancer or tumor of colon or stomach may be diagnosed. The expression amount of the gene may be measured by measuring the amount of the mRNA transcribed from the gene or the amount of the cDNA prepared by using the mRNA as a template, or by measuring the enzyme produced in the sample cells by an immunoassay using the antibody of the present invention. The measurement of the mRNA or cDNA may be carried our using the above-described nucleic acid for measurement according to the present invention by the method described above.

EXAMPLES

The present invention will now be described concretely by way of examples thereof.

Example 1

Cloning and Sequencing Enzyme Gene and Expression Thereof

1. Search of Gene Database and Determination of Nucleotide Sequence of β3Gn-T6

Using analogous genes such as known β1,3-N-acetylglucosaminyltransferase genes, β1,3-galactosyltransferase genes (AF117222, Y15060, Y15014, AB026730, AF145784 and AF145784), and β1,3-N-acetylgalactosaminyltransferase gene (Y15062), search of analogous genes was carried out on a gene database. The used sequences were β1,3-N-acetylglucosaminyltransferase genes with accession Nos. (Gene Bank): AB049584, AB049585, AB049586 and AB045278; β1,3-galactosyltransferase genes of accession Nos. AF117222, Y15060, Y15014, AB026730, AF145784 and AF145784; and β1,3-N-acetylgalactosaminyltransferase gene with accession No. Y15062. The search was carried out using a program such as Blast [Altschul et al., J. Mol. Biol. 215, 403-410(1990)].

As a result, EST sequences with GenBank Accession Nos. AW182889 and AW192172 were discovered. Further, a genomic sequence with GenBank accession No. AP000752.3 was found, and it was discovered that the above-described two ESTs were identical. However, translation initiation site was not found. Therefore, cloning was performed using Marathon cDNA from colon and stomach from CLONTECH.

More particularly, PCR (a cycle of 94° C. for 20 seconds, 64° C. for 30 seconds and 72° C. for 2 minutes was repeated 30 times) was performed using the AP1 primer (adaptors designated AP1 and AP2 are attached to the both ends of DNA fragment) included in Marathon cDNA kit and a primer GP61 (ctccagacac atgcccatgt aggc) (SEQ ID NO: 3) set within the discovered sequence. Further, nested PCR (a cycle of 94° C. for 20 seconds, 66° C. for 30 seconds and 72° C. for 2 minutes was repeated 25 times) was carried out using the AP2 primer included in Marathon cDNA kit and a primer β3Gn-T6-RACE-06 (gtcgtcgtcg ccgctgagca gaaa) (SEQ ID NO: 4). The desired fragment was cut out from the gel and purified by a conventional method, followed by sequencing (SEQ ID NO: 2)

2. Incorporation of β3Gn-T6 into Expression Vector

To prepare an expression system of β3Gn-T6, β3Gn-T6 gene was first incorporated into pFastBac of Gateway system from INVITROGEN, and then a Bacmid by Bac-to-Bac system from INVITROGEN was prepared. These operations will now be described in detail.

Incorporation into pFastBac by Gateway System

①. Preparation of Entry Clone

A DNA fragment was again obtained by POR (a cycle of 94° C. for 20 seconds, 66° C. for 30 seconds and 72° C. for 2 minutes was repeated 35 times) using Marathon cDNA as a template and primer F (β3Gn-T6-02:5'-ggggacaagt ttgtacaaaa aagcaggctt ccaggaggag acgccagagg g-3') (SEQ ID NO: 5) and primer R (β3Gn-T6-03:5'ggggaccact ttgtacaaga aagctgggtc tggcctcagg agacccggtg-3') (SEQ ID NO: 6). The desired fragment was cut out from the gel and purified. The fragment was then incorporated into pDONR201 by BP clonase reaction to prepare an "entry clone". The reaction was carried by incubating a mixture of 5 µl of the desired DNA fragment, 1 µl (150 ng) of pDONR201, 2 µl of reaction buffer and 2 µl of BP clonase mix at 25° C. for 1 hour. After adding 1 µl of Proteinase K, the reaction mixture was left to stand at 37° C. for 10 minutes, thereby terminating the reaction.

Then the whole mixture (11 µl) was mixed with 100 µl of competent cells (*E. coli* DH5α), and after heat shock, the mixture was plated on an LB plate containing kanamycin. On the next day, colonies were collected, and existence of the desired DNA was directly confirmed by PCR, followed by extraction and purification of the vector (pDONR-β3Gn-T6).

② Preparation of Expression Clone

The above-described entry clone has attL at the both ends of the inserted region, the attL being a recombination site used when λ phage is cut out from *E. coli*. By mixing the entry clone with LR clonase (a mixture of recombination enzymes Int, IHF and Xis of λ phage) and a destination vector, the inserted region is transferred to the destination vector so that an expression clone is prepared. These operations will now be described in detail.

Firstly, a mixture of 1 µl of the entry clone, 0.5 µl (75 ng) of pFBIH, 2 µl of LR reaction buffer, 4.5 µl of TE and 2 µl of LR clonase mix were allowed to react at 25° C.for 1 hour, and then 1 µl of Proteinase K was added, followed by incubation at 37° C.for 10 minutes, thereby terminating the reaction (by this recombination reaction, pFBIH- β3Gn-T6 is generated). The pFBIH was one obtained by inserting Igk signal sequence (MHFQVQIFSFLLISASVIMSRG) (peptide of SEQ ID NO: 7) and His tag (6 His) into pFastBac 1. The DNA fragment obtained by PCR using OTS (5'gatcatgcattttcaagtgcagattttcagcttcctgctaatcagtgcctcagtcataa tgtcacgtggacatcaccatcaccatcac3') (SEQ ID NO: 7) as a template and primer OT20 (5'cgggatccat gcattttcaa gtgcag3') (SEQ ID NO: 8) and OT22 (5'-ggaattcgtgatggtgatggtgatg-3') (SEQ ID NO: 9) was inserted using Bam HI and Eco RI. Further, to insert the Gateway sequence, Conversion cassette was inserted using Gateway Vector Conversion System (INVITROGEN). The Igk signal sequence was inserted in order to change the expressed protein to a secretory protein, and the His tag was inserted for purification.

Then the whole mixture (11 µl) was mixed with 100 µl of competent cells (*E. coli* DH5α), and after heat shock, the mixture was plated on an LB plate containing ampicillin. On the next day, colonies were collected, and existence of the desired DNA was directly confirmed by PCR, followed by extraction and purification of the vector (pFBIH-β3Gn-T6).

The same experiment was repeated except that pFBIH was replaced with pFBIF. In pFBIF, FLAG peptide (DYKD-DDDK) (residues 23-30 from the peptide sequence of SEQ ID NO: 10) was inserted for purification in place of His tag. The DNA fragment obtained by PCR using OT3 (5'gatcatgcattttcaagtgcagattttcagcttcctgctaatcagtgcctcagtcataat gtcacgtggagattacaaggacgacgatgacaag-3') (SEQ ID NO: 10) as a template and primer OT20 (the sequence is described above) and OT21 (5'-ggaat tcttgt catcg tcgtc cttg-3') (SEQ ID NO: 11) was inserted using Bam HI and Eco RI. Further, to insert the Gateway sequence, Conversion cassette was inserted using Gateway Vector Conversion System (INVITROGEN).

Preparation of Bacmid by Bac-to-Bac System

Using Bac-to-Bac system (INVITROGEN), recombination was carried out between the above-described pFBIH-β3Gn-T6 or pFBIF-β3Gn-T6 and pFastBac, the 3Gn-T6 and other sequences were inserted into a Bacmid which was able to replicate in insect cells. With this system, the desired gene is incorporated into the Bacmid by the recombinant protein produced by a helper plasmid, only by incorporating pFastBac into which the desired gene was inserted, using the recombination site of Tn7 into an E. coli (DH10BAC) containing the Bacmid. The Bacmid contains lacZ gene, so that classical selection based on the color, that is, blue (no insertion) or white (with insertion), of the colony can be attained.

That is, the above-described purified vector (pFBIH-beta3GnT-6 or pFBIF-β3Gn-T6) was mixed with 50 µl of competent cells (E. coli DH10BAC), and after heat shock, the mixture was plated on an LB plate containing kanamycin, gentamycin, tetracycline, Bluo-gal and IPTG. On the next day, white single colony was further cultured and Bacmid was collected.

3. Introduction of Bacmid into Insect Cells

After confirming that the desired sequence was inserted into the Bacmid obtained from the white colony, the Bacmid was introduced into insect cells Sf21 (commercially available from INVITROGEN). That is, to a 35 mm Petri dish, Sf21 cells in an amount of 9 ×$10^5$ cells/2 ml (Sf-900SFM (INVITROGEN) containing an antibiotic) were added, and the cells were cultured at 27° C. for 1 hour to adhere the cells. (Solution A): To 5 µl of the purified Bacmid DNA, 100 µl of Sf-900SFM (INVITROGEN) not containing an antibiotic was added. (Solution B): To 6 µl of CellFECTIN Reagent (INVITROGEN), 100 µl of Sf-900SFM (INVITROGEN) not containing an antibiotic was added. Solution A and Solution B were then gently mixed and the mixture was incubated for 15 to 45 minutes at room temperature. After confirming that the cells adhered, the culture medium was aspirated and 2 ml of Sf-900SFM (INVITROGEN) not containing an antibiotic was added. To a solution (lipid-DNA complexes) prepared by mixing Solution A and Solution B, 800 µl of Sf900II not containing an antibiotic was added and the resultant was gently mixed. The culture medium was aspirated, and diluted lipid-DNA complexes solution was added to the cells, followed by incubating the cells at 27° C. for 5 hours. Thereafter, transfection mixture was removed and 2 ml of culture medium Sf-900SFM (INVITROGEN) containing an antibiotic was added, followed by incubating the resultant at 27° C. for 72 hours. Seventy two hours after the transfection, the cells were peeled off by pipetting, and the cells and the culture medium were collected. The cells and the culture medium were centrifuged at 3000 rpm for 10 minutes, and the obtained supernatant was stored in a separate tube (this supernatant is the primary virus solution).

To a T75 culture flask, Sf21 cells in an amount of 1×$10^7$ cells/20 ml of Sf-900SFM (INVITROGEN) (containing an antibiotic) were placed, and the resultant was incubated at 27° C. for 1 hour. After the cells adhered, 800 µl of the primary virus was added and the resultant was cultured at 27° C. for 48 hours. Forty eight hours later, the cells were peeled off by pipetting and the cells and the culture medium were collected. The cells and the culture medium were centrifuged at 3000 rpm for 10 minutes, and the obtained supernatant was stored in a separate tube (this supernatant was used as the secondary virus solution).

Further, to a T75 culture flask, Sf21 cells in an amount of 1×$10^7$ cells/20 ml of Sf-900SFM (INVITROGEN) (containing an antibiotic) were placed, and the resultant was incubated at 27° C. for 1 hour. After the cells adhered, 1000 µl of the secondary virus solution was added and the resultant was cultured at 27° C. for 72 to 96 hours. After the culturing, the cells were peeled off by pipetting and the cells and the culture medium were collected. The cells and the culture medium were centrifuged at 3000 rpm for minutes, and the obtained supernatant was stored in a separate tube (this supernatant was used as the tertiary virus solution).

Further, to a 100 ml spinner flask, 100 ml of Sf21 cells at a population of 6×$10^5$ cells/ml was placed, and 1 ml of the tertiary virus solution was added, followed by culturing the cells at 27° C. for about 96 hours. After the culturing, the cells and the culture medium were collected. The cells and the culture medium were centrifuged at 3000 rpm for 10 minutes, and the obtained supernatant was stored in a separate tube (this supernatant was used as the quaternary virus solution).

The primary to tertiary cell pellets were sonicated (sonication buffer: 20 mM HEPES pH 7.5, 2% Triton X-100) and the crude cell extract was 20-fold diluted with $H_2O$. The resultant was subjected to SDS-PAGE and then to Western blotting to confirm the expression of β3Gn-T6 protein. As the antibody, a monoclonal antibody 6-His (MMS-156P, COVANCE) was used for beta3GnT-6 to which the histidine tag was attached, and anti-FLAG M2-peroxidase (A-8592, SIGMA) was used for β3Gn-T6 to which the FLAG sequence was attached.

Bands of both 6His-β3Gn-T6 and FLAG-β3Gn-T6 were observed at the positions of 40 K and 45 K.

4. Resin Purification of β3Gn-T6

From the above-described tertiary infection bottle, quaternary infection was carried out, and pellets and supernatants were collected from the both bottles. After centrifugation (5000 rpm for 10 minutes, twice), the pellets were sonicated (sonication buffer: 20 mM HEPES pH 7.5, 2% Triton X-100), and the protein in the crude pellet extracts and in the supernatants was quantified (DC Protein Assay Kit, BIO-RAD). After adjusting the amount of the protein, they were subjected to SDS-PAGE and Western blotting to confirm the expression of β3Gn-T6. Based on the results, the supernatant of FLAG-β3Gn-T6 of which relative amount of expression was the largest was used for the purification.

To 10 ml of the supernatant of FLAG-β3Gn-T6 of quaternary infection, $NaN_3$ (0.05%), NaCl (150 mM), $CaCl_2$ (2 mM), and anti-M1 resin (SIGMA) (50 µl) were added and the resulting mixture was stirred overnight at 4° C. On the next day, the mixture was centrifuged (3000 rpm for 5 minutes, at 4° C.) and the pellet was collected. To the pellet, 900 µl of 2 mM CaCl2·TBS was added and the resultant was centrifuged again (2000 rpm for minutes, at 4° C.), and the pellet was suspended in 200 µl of 1 mM $CaCl_2$·TBS to obtain a sample (beta3GnT-6 enzyme solution) for the measurement of activity.

5. Search of Acceptor Substrate of β3Gn-T6

As a result of molecular evolutionary analysis comparing β3Gn-T6 with 1,3-N-acetylglucosaminyltransferases and β1,3-galactosyltransferases, 3Gn-T6 was classified into β1,3-N-acetylglucosaminyltransferases. Thus, firstly, analysis was performed using UDP-GlcNAc as the donor substrate.

Using the following reaction systems, the acceptor substrate was searched. As the "acceptor substrate" in the reaction solution described below, each of the following was used and whether each of them functioned as the acceptor or not was investigated: pNp-α-Glc, pNp-β-Glc, pNp-αGlcNAc, pNp-β-GlcNAc, pNp-α-Gal, pNp-β-Gal, pNp-α-GalNAc, pNp-α-Xyl, pNp-β-Xyl, pNp-α-Fuc, Bz-α-Man, Bz-α-ManNAc, LacCer, GalCertypeI and Bz-β-lactoside (all of them are from SIGMA).

The reaction solution (the numbers in the parentheses indicate the final concentrations) contained acceptor substrate (10 nmol), sodium cacodylate buffer (pH7.2)(50 mM), $MnCl_2$ (10 mM), UDP-GlcNAC (480 μM) and UDP-[$^{14}$C] GlcNAC (175 nCi), to which 5 μl of the β3Gn-T6 enzyme solution and $H_2O$ were added to attain a final volume of 25 μl.

The reaction mixture was allowed to react at 37° C. for one day and night, and after completion of the reaction, 200 μl of $H_2O$ was added, followed by light centrifugation and collection of the supernatant. The supernatant was passed through Sep-Pak plus C18 Cartridge (Waters) equilibrated by washing once with 10 ml of methanol and then twice with 10 ml of $H_2O$, so as to adsorb the substrate and the product in the supernatant on the cartridge. After washing the cartridge twice with 10 ml of $H_2O$, the adsorbed substrate and the product were eluted with 5 ml of methanol. The eluted solution was evaporated to dryness by blowing nitrogen gas while heating the solution with a heat block at 40° C. To the resultant, 20 μl of methanol was added, and the resulting mixture was plotted on a TLC plate (HPTLC plate Silica gel 60: MERCK), and developed using a developing solvent having the composition of chloroform:methanol:water (containing 0.2% $CaCl_2$) =65:35:8. After developing the mixture up to 5 mm from the top end of the TLC plate, the plate was dried and the intensity of the radioactivity taken in the product was measured using Bio Image Analyzer FLA3000 (FUJI PHOTO FILM).

As a result, pNp-β-Gal very slightly reacted, and strong reaction was indicated for pNp-α-GalNAc, so that it was suggested that β3Gn-T6 is a synthetase of N-acetylglucosaminyl β1,3-acetylgalactosaminyl α1-R.

6. Confirmation of Activity Using N-acetylgalactosaminyl-serine (GalNAcα1-Ser) as Acceptor Substrate Since it was suggested that β3Gn-T6 is a synthetase of core 3 sugar chain (N-acetylglucosaminyl β1,3-N-acetylgalactosaminylα1-R), the above-described experiment was carried out again using GalNAcα1-Ser as the acceptor substrate. As a result, a strong reaction similar to that for GalNAcα-pNp was observed, so that it was indicated that β3Gn-T6 is a novel synthetase of core 3 sugar chains. More particularly, the amino acid residue Ser in GalNAcα1-Ser was labeled with Cy5 label (Cy5 Reactive Dye Pack, AMERSHAM PHARMACIA BIOTHECH), and Cy5-labeled GalNAcα1-Ser was collected after HPLC (using C18 column) using the fluorescence from Cy5 as an index. The obtained Cy5-labeled GalNAcα1-Ser was used as the acceptor substrate after freeze drying. The reaction system was the same as in Example 5. After completion of the reaction, 10 μl of the reaction solution was analyzed by HPLC. With the reaction solution to which the donor substrate (UDP-GlcNAc) was added, a peak for the Cy5 labeled GalNAcα1-Ser (acceptor substrate) was detected. On the other hand, with the reaction solution to which the donor substrate was added, the peak of the acceptor substrate and a new peak were detected. Thus, β3Gn-T6 exhibited the activity to transfer GlcNAc to GalNAc of GalNAcα1-Ser.

7. Analysis of Manner of Binding Between N-acetylglucosamine and N-acetylgalactosaminylα1-R The reaction solution contained 50 mM HEPES buffer, 10 mM $MnCl_2$, 0.1% Triton-CF54, 1 mM pNp-α-GalNAc and 1.5 mM UDP-GlcNAc, to which 5 μl of β3Gn-T6 was added, so as to have a total volume of 20 μl. The reaction was carried out at 37° C. for 16 hours. After completion of the reaction, analysis was carried out using HPLC. The column used was Mightysil RP-18, 250×4 mm, the solvent was acetonitrile: $H_2O$=10:90, and the detection was carried out in terms of the absorption at 210 nm. As standard samples, GlcNAcβ1-3GalNAcα-pNp (core 3 structure) and GlcNAcβ1-6GalNAcα-pNp (core 6 structure) were used (SIGMA). As a result, as for the standard samples, GalNAcα-pNp was eluted at 23.5 minutes, GlcNAcβ1-3GalNAcα-pNp was eluted at 18.6 minutes and GlcNAcβ1-6GalNAcα-pNp was eluted at 20 minutes. As for the β3Gn-T6 solution, the peak at 23.5 minutes (GalNAcα-pNp) and the peak at 18.6 minutes (GlcNAcβ1-3GalNAcα-pNp) were observed. Thus, β3Gn-T6 is a novel enzyme having an activity to transfer N-acetylglucosamine to a non-reducing terminal of N-acetylgalactosaminyl group through the β1,3-linkage.

8. Expression in Various Cell Lines Total RNAs were extracted from various cell lines and cDNAs were prepared by the conventional method. Expression of the enzyme gene was examined by PCR using the cDNAs. The primers used were GP- 57(5'gcctacatgggcatgtgtctggag3') (SEQ ID NO: 12) and GP60(5'agagctgggc aggacgtaag gtac-3') (SEQ ID NO: 13). The used enzyme was AmpliTaq Gold (APPLIED BIOSYSTEMS). A cycle of 95° C. for 30 seconds, 64° C. for 30 seconds and 72° C. for 30 seconds was repeated 45 times, and the amplification product was detected by electrophoresis on 2% agarose gel. The expected PCR product had a size of 323 bases. When an amplification product having this size was observed, the expression was marked "+" and when the amplification product was not observed, the expression was marked "+". The amplification product was observed as a single band, and no other amplification products were observed. Some of the amplification products were treated with a restriction enzyme to confirm that the amplification product was originated from β3Gn-T6 gene. The results are shown in Table 1 below.

TABLE 1

| Cell Name | Type | Expression |
|---|---|---|
| Colo205 | colon | − |
| HL60 | leukemia | − |
| HCT15 | colon | − |
| MKN45 | stomach | − |
| KATO III | stomach | + |
| LSC | colon | + |
| LSB | colon | − |
| HepG2 | liver | + |
| GOTO | neuroblastoma | − |
| T98G | gliablastoma | + |
| PC-1 | lung squamous cell | + |
| PC-7 | lung adenocarcinoma | − |
| SW480 | colon | − |
| SW1116 | colon | + |
| EBC-1 | lung epithelial cell | + |
| Lu130 | lung small cell | + |
| HSC43 | stomach | − |
| A431 | esophagus | + |
| SCCH-26 | neuroblastoma | − |
| U251 | gliablastoma | + |
| Capan-2 | pancreas | − |
| PA-1 | uterus | − |

TABLE 1-continued

| Cell Name | Type | Expression |
|---|---|---|
| Namalwa | B cell leukemia | + |
| Daudi | B cell (Burkitt's) | − |
| Jurkat | T cell leukemia | − |
| U937 | T cell leukemia | + |
| U266 | monocyte | + |
| K562 | myeloma | + |

9. Expression in Normal Tissues Expression of the enzyme gene was examined for normal human tissues using Marathon cDNA (CLONTECH) of each tissue. The primers used were GP57(5'-gcctacatgggcatgtgtctggag-3') (SEQ ID NO: 12) and GP-60(5'-agagctgggc aggacgtaag gtac-3') (SEQ ID NO: 13). The used enzyme was LA Taq (TaKaRa). A cycle of 95° C. for 20 seconds, 64° C. for 30 seconds and 72° C. for 30 seconds was repeated 30 times, and the amplification product was detected by electrophoresis on 1% agarose gel. The expected POR product had a size of 323 bases. When an amplification product having this size was observed, the expression was marked "+" and when the amplification product was not observed, the expression was marked "−". The results are shown in Table 2 below. The amplification product was observed as a single band, and no other amplification products were observed. The tissues in which the enzyme gene was expressed were esophagus, stomach and colon.

Expression of the enzyme gene was examined for normal human tissues using Marathon cDNA (CLONTECH) of each tissue. The primers used were GP-57(5'-gccta-catgggcatgtgtctggag-3') and GP-60(5'-agagctgggc aggacg-taag gtac-3'). The used enzyme was LA Taq (TaKaRa). A cycle of 95° C. for seconds, 64° C. for 30 seconds and 72° C. for 30 seconds was repeated 30 times, and the amplification product was detected by electrophoresis on 1% agarose gel. The expected PCR product had a size of 323 bases. When an amplification product having this size was observed, the expression was marked "+", and when the amplification product was not observed, the expression was marked "−". The results are shown in Table 2 below. The amplification product was observed as a single band, and no other amplification products were observed. The tissues in which the enzyme gene was expressed were esophagus, stomach and colon.

TABLE 2

| Tissue | Expression |
|---|---|
| aorta | − |
| bone marrow | − |
| bladder | − |
| whole blood | − |
| colon | + |
| heart | − |
| kidney | − |
| promyelocytic leukemia cell | − |
| leukocyte | − |
| liver | − |
| lung | − |
| lac gland | − |
| melanoma | − |
| ovary | − |
| pancreas | − |
| placenta | − |
| small intestine | − |
| spleen | − |
| stomach | + |

TABLE 2-continued

| Tissue | Expression |
|---|---|
| testis | − |
| thymus | − |
| uterus | − |
| esophagus | + |

Example 2

Preparation of Anti-enzyme Monoclonal Antibody (1) Immunization of Mice

The His-β3Gn-T6 protein obtained in Example 1 was purified by using a column in which TALON (trademark) CellThru (CLONTECH) beads were packed and the purified protein was used as an antigen. An antigen emulsion for immunization, prepared by a conventional method, was subcutaneously administered to mice, and three boosters were administered at two weeks' interval.

(2) Preparation of Myeloma Cells

Myeloma cell P3X63Ag8U1 was used. The culture of the cells was started one week before the cell fusion so that 5 to $10 \times 10^7$ cells could be obtained at the day of cell fusion. On the day of cell fusion, the cells were centrifuged at 4° C. at 1200 rpm for 5 minutes. To the pellet, RPMI 1640 was added and the cells were suspended again, followed by centrifugation. The cells were suspended again in 20 ml of RPMI 1640 and the number of cells was counted.

(3) Preparation of Spleen Cells

The spleens removed from the two immunized mice were placed on a stainless steel mesh and cells were scraped out, and the stainless steel mesh was washed with RPMI 1640 (GIBCO) so as to drop the cells on a culture plate. The cell suspension was filtered through a glass wool, and the filtrate was centrifuged at 4° C. at 1000 rpm for 5 minutes to collect the cells. To the cells, 40 ml of RPMI 1640 was added and the number of cells was counted.

(4) Cell Fusion

The myeloma cells and the spleen cells were mixed at a ratio of 1:5, and the cells were centrifuged at 4° C. at 1000 rpm for minutes. The supernatant was removed and 1 ml of PEG-Eagle MEM was slowly added to loosen the cells, and then 30 ml of RPMI 1640 at 37° C. was slowly added. After centrifugation (800 rpm, room temperature, 5 minutes), the supernatant was removed, and 10 ml of 10% FCS+RPMI 1640 at 37° C. was added. After leaving the resultant to stand at 37° C. for 60 minutes, the tube was capped and was slowly shaken upside down so as to loosen the pellet. To the resultant, 40 ml of 10% FCS+RPMI-1640 was added and the resultant was poured in fraction of 25 ml each, followed by addition of 10% FCS+RPMI-1640 to a volume of 50 ml each. Using a crystal tip of which tip was cut, 100 μl each of the resultant was placed in each of the wells of 10 96-well plates, and the cells were cultured overnight at 37° C.

(5) HAT Selection

On the next day of cell fusion, 50×HAT (SIGMA) was added to 10% FCS+RPMI-1640 to prepare 2×HAT, and 100 μl of the prepared medium was added to each well in an amount of 100 μl/well. Thereafter, the medium was replaced by 100 μl each at two or three days' interval.

(6) Screening and Cloning

From 10 days after the cell fusion, screening was started by ELISA using the expressed protein His-beta3Gn-T6 obtained in Example 1 as an antigen. The ELISA was carried out as follows: The His-β3Gn-T6 purified by using a column in which TALON (trademark) CellThru (CLONTECH) beads were packed was dissolved in phosphate-buffered physiological saline (PBS) to a concentration of 1 μg/ml, and the obtained solution was added to the wells of 96-well plates in an amount of 50 μl/well, followed by leaving the plates to stand at 4° C. for 16 hours. Thereafter, the wells were washed three times with physiological saline in an amount of 300 μl/well. To each well, 200 μl of Block Ace (DAINIPPON PHARMACEUTICAL) 4-fold diluted with purified water was added, and the resultant was incubated at 37° C. for 1 hour. Then the wells were washed three times with physiological saline in an amount of 300 μl/well. To each well, 50 μl of the culture supernatant was added, and the resultant was incubated at 37° C. for 1 hour. Thereafter, the wells were washed three times with physiological saline in an amount of 300 μl/well. To each well, 50 μg/ml of anti-mouse immunoglobulin goat polyclonal antibody labeled with alkaline phosphatase (DACO) was added in an amount of 50 μl/well, and the resultant was incubated at 37° C. for 1 hour. Thereafter, the wells were washed three times with physiological saline in an amount of 300 μl/well. For coloring, ALP Rose Shino-test (SHINO-TEST) was used. To each well, the substrate solution was added in an amount of 50 μl/well and the resultant was left to stand at room temperature for minutes. Then the coloring solution was added in an amount of 50 μl/well, and the absorbance at 510 to 620 nm was measured. When the absorbance was not less than 0.1, the result was judged as positive.

As a result, 126 positive wells were observed in 960 wells. Using the 126 types of the culture supernatant, immunostaining was performed using a colon tissue specimen, and Western blotting was performed using FLAG-β3Gn-T6 as an antigen. The immunostaining was performed by the DAB method (ENVISION+kit/HRP (DAB)-universal (mouse), DACO) employed in general, as follows: The colon tissue was fixed with formalin and paraffin sections were prepared by the conventional method. The sections were immersed in an endogenous peroxidase-blocking reagent at room temperature for 30 minutes. Then the specimens were immersed in Tris buffered physiological saline (TBS) at room temperature for 5 minutes after washing off the reagent with TBS. To each section, 100 μl of each culture supernatant was added, and the resultant was incubated overnight at 4° C. Thereafter, the culture supernatant was washed off with TBS, and each section was immersed in TBS (5 minutes, 3 times), thereby washing the section. Then EVISION+polymer reagent was dropped on the section and the resultant was incubated at room temperature for 60 minutes. Thereafter, the reagent was washed off with TBS, and each section was immersed in TBS (5 minutes, 3 times), thereby washing the section. Each section was immersed in diaminobenzidine for 10 minutes stationarily. The reagent was washed off with purified water and each section was immersed in purified water. Then each section was immersed in hematoxylin solution for 7 seconds, and then washed with flowing water. Each section was dehydrated, penetrated and encapsulated, and then observed with a microscope. Western blotting was carried out as follows: FLAG-beta3Gn-T6 was electrophoresed by SDS-PAGE, and the band was transferred to a PVDF membrane. The membrane was blocked with Block Ace 4-fold diluted with purified water. The PVDF membrane was cut into thin rectangles, and each PVDF membrane was immersed in a culture medium at room temperature for 1 hour. Each membrane was washed three times with PBS containing 0.1% Tween-20. To each membrane, 50 μg/ml of anti-mouse immunoglobulin goat polyclonal antibody labeled with peroxidase (DACO) was added, and the resultant was allowed to react at room temperature for 1 hour. Thereafter, each membrane was washed twice with PBS containing 5% Tween-20 and once with PBS. Coloring was performed using immunostain HRP-1000 kit (KONICA).

As a result, positive reaction was observed for 3 types of cells. The thus selected 3 types of hybridoma cells were subjected to cloning by limiting dilution method. That is, the hybridomas were diluted to a cell population of 0.3 cell/well, and then cultured for 10 days. After confirming that one well contained one colony under microscope, the culture supernatants were screened for the positive colonies by the above-described ELISA. This operation was repeated again, to obtain two clones which produce anti-beta3Gn-T6 antibody. One of the hybridomas of the obtained two clones was designated MA-136 G8 NO.144'02.10.1 and deposited with International Patent Organism Depositary, National Institute of Advanced Industrial Science and Technology under the Budapest Treaty. The accession No. is FERM BP-8200.

Example 3

Confirmation of Reactivity of Monoclonal Antibody

The above-described monoclonal antibody-producing cells (FERM BP-8200) were intraperitoneally administered to BALB/c mice and nude mice. Two weeks later, ascites were collected and subjected to sedimentation with 30% ammonium sulfate and to dialysis against PBS. Thereafter, the immunological reactivity was confirmed by Western blotting and histoimmunostaining as described in Example 2. As a result, strong reactivities to mucosal epithelial cells in colon and stomach were observed.

Example 4

Detection of Cancers and Tumors Using Monoclonal Antibody

Using the above-described monoclonal antibody (FERM BP-8200), staining of stomach cancer, colon cancer and familial colonic polyposis was carried out as in Example 2. As a result, staining with the monoclonal antibody to beta3G-T6 was observed in the normal tissues of stomach and colon. It was confirmed that 3Gn-T6 expressed in the region of Golgi body in the mucosal epithelial cells in stomach, and in the region of Golgi body in beaker cells in mucosa of colon. In the tissues of stomach cancer and colon cancer, β3Gn-T6 completely disappeared.

The tissue of familial colonic polyposis was classified into Groups 1 to 5 based on the grade of atypism. The classification criteria of Groups 1-5 are as follows:

roup 1: normal tissue, and benign (non-tumorous) lesion not exhibiting atypism

Group 2: lesion exhibiting atypism but judged to be benign (non-tumorous)

Group 3: lesion at the boundary between benign (non-tumorous) and malignant

Group 4: lesion for which cancer is strongly suspected

Group 5: cancer

In the tumorous polyp region of Group 4 or more, β3Gn-T6 completely disappeared. The results of the histostaining are shown in Table 3 below.

TABLE 3

| | No. | | Result of Staining |
|---|---|---|---|
| stomach | MK273 | adenocarcinoma | − |
| | MK285 | signet ring cell carcinoma | − |
| | MK295 | adenocarcinoma + undifferentiated carcinoma | − |
| | MK303 | undifferentiated carcinoma | − |
| colon | RK178 | adenocarcinoma | − |
| | RK279 | adenocarcinoma | + |
| | RK289 | adenocarcinoma | − |
| | RK299 | undifferentiated carcinoma | − |
| familial colonic polyposis | 1-1 | Group 2-3 | ++ |
| | 1-2 | Group 4-5 | − |
| | 1-3 | Group 4-5 | − |
| | 1-4 | Group 4-5 | − |
| | 1-5 | Group 1-2 | ++ |
| | 1-6 | Group 2-3 | ++ |
| | 1-7 | Group 3 | + |
| | 1-8 | Group 1-2 | ++ |
| | 1-9 | Group 2-3 | ++ |
| | 1-10 | Group 2.5 | ++ |
| | 1-11 | Group 3.5-4 | − |
| | 1-12 | Group 2 | ++ |
| | 1-13 | Group 3.5-4 | ++−− |
| | 1-14 | normal | ++ |
| | 1-15 | normal | ++ |
| | 1-16 | normal | ++ |
| | 1-17 | Group 3 | ++−+ |
| | 1-18 | Group 3.5 | − |
| | 1-19 | Group 3.5-4 | − |
| | 1-20 | Group 2 | ++ |
| | 1-21 | normal | ++ |
| | 1-22 | Group 2-3.5 | ++−− |
| | 1-23 | Group 4 | − |
| | 1-24 | normal | ++ |
| | 1-25 | Group 2 | ++ |
| | 1-26 | normal | ++ |
| | 1-27 | normal | ++ |
| | 1-28 | Group 2-3 | ++ |
| | 1-29 | Group 3-4 | ++ |
| | 1-30 | Group 2 | ++ |
| | 1-31 | Group 3.5-4 | ++ |
| | 1-32 | Group 1.5 | ++ |
| | 1-33 | Group 2.5-3 | ++ |

−: staining was not observed
+: staining was observed
++: strong staining was observed

The invention claimed is:

1. An isolated protein having the amino acid sequence shown in SEQ ID NO: 1, or an isolated protein having a homology of not less than 95% to said amino acid sequence shown in SEQ ID NO:1, which has an activity to transfer N-acetylglucosamine to a non-reducing terminal of N-acetylgalactosaminyl group through a β1,3-linkage.

2. The protein according to claim 1, wherein said protein has an amino acid sequence having the same amino acid sequence as shown in SEQ ID NO: 1 except that one or several amino acids are substituted or deleted, or that one or several amino acids are inserted or added, and wherein said protein has a homology of not less than 95% to the amino acid sequence shown in SEQ ID NO: 1.

3. The protein according to claim 2, which has the amino acid sequence shown in SEQ ID NO:1.

* * * * *